United States Patent [19]

Kasahara et al.

[11] 4,292,404
[45] Sep. 29, 1981

[54] METHOD FOR DETERMINING THE ACTIVITY OF THE ANGIOTENSIN-CONVERTING ENZYME

[75] Inventors: Yasushi Kasahara, Tama; Yoshihiro Ashihara, Fuchu, both of Japan

[73] Assignee: Fujizoki Pharmaceutical Co., Ltd., Tokyo, Japan

[21] Appl. No.: 186,075

[22] Filed: Sep. 11, 1980

[30] Foreign Application Priority Data

Sep. 26, 1979 [JP] Japan ............................... 54-122562

[51] Int. Cl.³ ........................... C12Q 1/34; C12Q 1/28
[52] U.S. Cl. ...................................... 435/18; 435/24; 435/28; 424/7; 23/932
[58] Field of Search .............. 435/23, 24, 28, 13, 435/18, 19; 23/932; 424/7, 2; 260/112.5

[56] References Cited

U.S. PATENT DOCUMENTS 4,108,726 8/1978 Silverstein ........................... 435/24

OTHER PUBLICATIONS

Hayakari, M. et al.; "A Rapid and Simple Spectrophotometric Assay of Angiotensin-Converting Enzyme"; Anal. Bioch. (84), pp. 361–369 (1978).

Rohrbach, M. S.; Analytical Biochemistry (84), pp. 272–276 (1978).

Conroy J. M. et al.; "A Rapid and Sensitive Fluorescence Assay for Angiotensin-Converting Enzyme"; Anal. Bioch. (87), pp. 556–561 (1978).

Ryan J. W. et al.; "A Simple Radioassay for Angiotensin-Converting Enzyme"; Biochem Journal (167) pp. 501–504 (1977).

Primary Examiner—Benoît Castel
Attorney, Agent, or Firm—Blanchard, Flynn, Thiel, Boutell & Tanis

[57] ABSTRACT

Method for determining the activity of the angiotensin-converting enzyme comprising the steps of:
(1) mixing a liquid containing the angiotensin-converting enzyme with a reagent consisting essentially of X-hippuryl-L-histidyl-L-leucine, hippuricase, peroxidase, 4-aminoantipyrine and $H_2O_2$, and
(2) colorimetrically measuring the concentration of quinonimine dye produced in step (1).

4 Claims, No Drawings

METHOD FOR DETERMINING THE ACTIVITY OF THE ANGIOTENSIN-CONVERTING ENZYME

EXPLANATION OF THE INVENTION

The present invention relates to a method for determining the activity of the angiotensin-converting enzyme by using X-hippuryl-L-histidyl-L-leucine, as a synthetic substrate, and hippuricase.

The angiotensin-converting enzyme (hereinafter referred to as ACE for short) catalyzes the conversion of angiotensin I to angiotensin II through splitting off of carboxy-terminal dipeptide, i.e. L-histidyl-L-leucine, said angiotensin II being an active pressor substance.

The ACE plays an important role in the human body, and a diagnosis of sarcoidosis can be made by measuring the level of ACE in the blood.

The accurate determination of the ACE content in human blood is significant from physiological and clinical viewpoints. As the conventional methods for that determination, there are known (1) radioimmunoassay (2) fluorometric assay and (3) liquid chromatography-assisted assay. However, such conventional methods have not been commonly employed, since such methods require special instruments. Spectrophotometric assay for ACE (one of the conventional methods) proposed by D. W. Cushman et al is known, and the procedure thereof is as follows:

Hippuryl-L-histidyl-L-leucine, which is used as a synthetic substrate, is added to the specimen containing ACE, such as human serum or humor, and permitted to react for a fixed time. The reaction is then stopped by adding HCl to the reaction system. Hippuric acid produced in the reaction is extracted with ethyl acetate from the reaction mixture. The residue obtained by evaporation of ethyl acetate is dissolved in distilled water. The concentration of hippuric acid is determined by measuring the ultraviolet absorption. The ACE activity can be evaluated from the concentration of hippuric acid thus found.

It is an object of the present invention to provide a simpler method for the determination of ACE activity.

The principle of this method is as follows:

In this method, X-hippuryl-L-histidyl-L-leucine having the following general formula is used as a synthetic substrate and hippuricase is used as an enzyme for decomposing hippuric acid to benzoic acid and glycine:

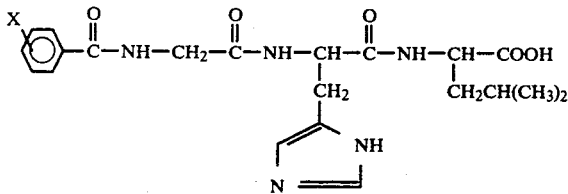

wherein X represents OH, NH$_2$ or N(CH$_3$)$_2$.

X-hippuryl-L-histidyl-L-leucine is added to a liquid containing ACE, such as human blood or humor, to produce X-hippuric acid and L-histidyl-L-leucine by decomposing the X-hippuryl-L-histidyl-L-leucine by the ACE. Hippuricase is added to the liquid to produce X-benzoic acid and glycine by decomposing the X-hippuric acid. Quinonimine dye is produced by the reaction of X-benzoic acid with 4-aminoantipyrine and H$_2$O$_2$ in the presence of peroxidase. The concentration of quinonimine dye is colorimetrically measured to evaluate the activity of ACE.

Therefore, the activity of ACE can be determined by the steps of:

(1) mixing a liquid containing ACE with a reagent consisting essentially of X-hippuryl-L-histidyl-L-leucine, hippuricase, peroxidase, 4-aminoantipyrine and H$_2$O$_2$, and (2) colorimetrically measuring the concentration of the quinonimine dye produced in step (1).

The principle of the method of the present invention is represented by the formulas as follows:

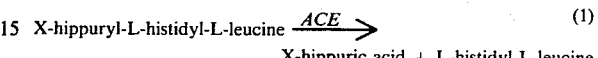
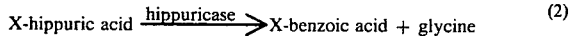
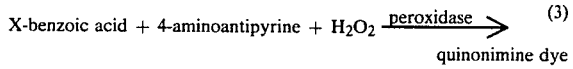

One of the synthetic substrates which is used in the present invention, p-hydroxyhippuryl-L-hystidyl-L-leucine, can be prepared as follows:

Synthesis of p-hydroxyhippuryl-L-histidyl-L-leucine:

30 g of carbobenzoxy-glycine and 24 g of L-histidine methyl ester are dissolved in 300 ml of chloroform and to this solution is added 30 g of ethylaminopropyl carbodiimide to be subjected to reaction. After the reaction mixture is allowed to stand at room temperature for two hours, it is washed by water and a 2.5% aqueous solution of NaHCO$_3$ and then the solvent (chloroform) is distilled off under reduced pressure.

25 g of the reaction product, carbobenzoxyglycyl-L-histidine methyl ester, is dissolved in 50 ml of ethanol, and to this solution is added 15 ml of hydrazine hydrate and then the solution is left to stand overnight. Carbobenzoxyglycl-L-histidine hydrazide thus produced is washed with water, and recrystallized from hot water.

21 g of carbobenzoxyglycyl-L-histidine hydrazide is dissolved in 185 ml of 1 N.HCl and to this solution is added 245 ml of ethyl acetate and 4.3 g of NaNO$_2$ at 0° C. with stirring, and after five minutes, 73 ml of a 50% aqueous solution of K$_2$CO$_3$ is added and then this solution is extracted with ethyl acetate. After the extract is dehydrated over anhydrous sodium sulfate, a solution (cooled to 0° C.) of L-leucine methyl ester in ethyl ether (9 g/208 ml) is added to the extract, and this mixture is left to stand overnight at −5° C. The crystals thus produced are filtered off, and washed with ethyl ether to obtain carbobenzoxyglycyl-L-histidyl-L-leucine methyl ester.

20 g of carbobenzoxyglycyl-L-histidyl-L-leucine methyl ester is added to 100 ml of 25% HBr solution in acetic acid and this mixture is stirred for one hour to split off the carbobenzoxy group, and then 2000 ml of absolute ether is added. The precipitate thus produced is filtered off and washed with ethyl ether and dried in a desiccator.

20 g of the precipitate, glycyl-L-histidyl-L-leucine methyl ester.2HBr, and 10.1 ml of triethylamine are dissolved in 80 ml of dichloromethane, and to this solution is added 6.5 g of p-acetoxybenzoic acid and then there is added 7.5 g of ethyl aminopropyl carbodiimide.HCl, and this mixture is stirred at room temperature for two hours. The reaction mixture is washed with water and a 2.5% aqueous solution of NaHCO$_3$, and then dried over anhydrous sodium sulfate, and freed of solvent under reduced pressure, and left to stand at a temperature of −20° C. to deposit p-acetoxyhippuryl-L-histidyl-L-leucine methyl ester.

5.1 g of p-acetoxyhippuryl-L-histidyl-L-leucine methyl ester is dissolved in 20 ml of methanol, and to this solution is added 20 ml of a 1 N.aqueous solution of NaOH at a temperature of 4° C., and after stirring for one hour, the pH of the solution is lowered to 5 by adding HCl, and water and methanol are distilled off. The residue is dissolved in methanol and filtered, and to this solution is added ethyl ether. The crystals deposited after standing at −20° C. are filtered to obtain p-hydroxyhippuryl-L-histidyl-L-leucine.

EXAMPLES

Examples of the present invention will be described below:

EXAMPLE 1

The activity of ACE was determined by using p-hydroxyhippuryl-L-histidyl-L-leucine, prepared as described above, as a synthetic substrate.

0.05 ml of serum and 0.049 ml of pure water were added to 0.25 ml of a buffer solution (pH 8.3) containing 5 mM of p-hydroxyhippuryl-L-histidyl-L-leucine, 1 U of hippuricase, 0.5 U of peroxidase, 2 mM of 4-aminoantipyrine, 2 mM of $H_2O_2$, 0.5 M of NaCl and 0.1 M of boric acid The variation of the absorbance by the solution was measured at 505 nm of light at a temperature of 37° C. during the course of the reaction. In the measurement, a centrifugal analyser was employed, in which the time lag was 5 seconds and the reaction time was 10 minutes. The activity unit (mU) of ACE is automatically printed out in the autoanalyzer. The calculation was performed according to the following formula:

$$mU = \frac{\text{Variation of absorbance at 505 nm}}{\text{Molecular absorptivity } (\epsilon)} \times$$
$$\frac{1}{\text{Reaction time (10 min)}} \times \frac{1}{\text{Light-path length (cm)}} \times$$
$$\frac{0.30}{0.05} \times 10^6$$

$\epsilon = 12000$ (Molecular absorptivity of quinonimine dye)

Results of the measurements, repeated 20 times, were as follows:
Activity unit (mU)=15.0±0.5 (nmol/ml/min);
Coefficient of variation (CV)=3.3%.

EXAMPLE 2

Activity unit (mU) and Coefficient of variation (CV) were obtained by repeating the same procedure and calculation as those of Example 1 except that 10 mM of p-aminohippuryl-L-histidyl-L-leucine was used instead of 5 mM of p-hydroxyhippuryl-L-histidyl-L-leucine, and the variation of the absorbance was measured at 480 nm and the calculation was performed by substituting 8000 for $\epsilon$.
Activity unit (mU)=16.0±0.28 (nmol/ml/min).
Coefficient of variation (CV)=1.8%.

EXAMPLE 3

Activity unit (mU) and Coefficient of variation (CV) were obtained by repeating the same procedure and calculation as those of Example 1 except that 8 mM of p-dimethylaminohippuryl-L-histidyl-L-leucine was used instead of 5 mM of p-hydroxyhippuryl-L-histidyl-L-leucine, and the variation of the absorbance was measured at 555 nm and the calculation was performed by substituting 32000 for $\epsilon$.
Activity unit (mU)=15.0±0.32 (nmol/ml/min).
Coefficient of variation (CV)=2.1%.

For the purpose of comparison with the method of the present invention, a measurement was carried out by Cushman's method, using the same serum as that used in the method of the present invention, and results of the measurement were obtained as follows:

0.1 ml of serum was added to 0.25 ml of a borate buffer solution (pH=8.3) containing 5 mM of hippuryl-L-histidyl-L-leucine and permitted to react at 37° C. for 60 minutes, and then the reaction was stopped by adding HCl to the solution. The hippuric acid produced was extracted with 1.5 ml of ethyl acetate, and the supernatant liquid was separated, and the residue on distillation of the solvent was dissolved in 2 ml of pure water. The absorbance of this liquid was measured at 228 nm to determine the amount of hippuric acid, and the activity unit of ACE (mU) was calculated. Results of the measurement repeated 20 times were as follows:
Activity unit (mU)=15.8±0.93.
Coefficient of variation (CV)=5.89%.

As can be seen in the results shown above, the method of the present invention is simple as compared with Cushman's method, and superior to it in reproducibility, as shown by their respective CV's. (CV's of the method of the present invention are 3.3%, 1.8% and 2.1%. CV of Cushman method is 5.89%.)

What is claimed is:

1. A method for determining the activity of the angiotensin-converting enzyme comprising the steps of:
   (1) mixing a liquid containing the angiotensin-converting enzyme with a reagent consisting essentially of X-hippuryl-L-histidyl-L-leucine having the formula

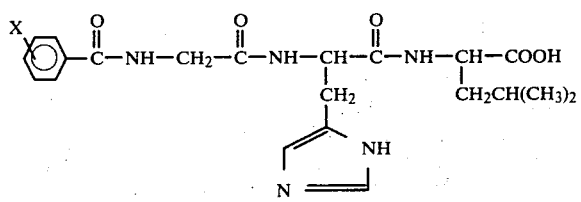

wherein X is OH, $NH_2$ or $N(CH_3)_2$, and with hippuricase, peroxidase, 4-aminoantipyrine and $H_2O_2$, under reaction conditions effective to form quinonimine dye, and
   (2) colorimetrically measuring the concentration of said quinonimine dye produced in step (1).

2. The method according to claim 1 wherein said X-hippuryl-L-histidyl-L-leucine is p-hydroxyhippuryl-L-histidyl-L-leucine.

3. The method according to claim 1 wherein said X-hippuryl-L-histidyl-L-leucine is p-aminohippuryl-L-histidyl-L-leucine.

4. The method according to claim 1 wherein said X-hippuryl-L-histidyl-L-leucine is p-dimethylaminohippuryl-L-histidyl-L-leucine.

* * * * *